United States Patent [19]
Tsukashima et al.

[11] Patent Number: 5,350,361
[45] Date of Patent: Sep. 27, 1994

[54] TRI-FOLD BALLOON FOR DILATATION CATHETER AND RELATED METHOD

[75] Inventors: Ross Tsukashima, San Diego; Matthew Jordan, Los Angeles; Gordon Jung, San Diego, all of Calif.

[73] Assignee: Medtronic, Inc., Minneapolis, Minn.

[21] Appl. No.: 150,673

[22] Filed: Nov. 10, 1993

[51] Int. Cl.[5] ............................................. A61M 29/00
[52] U.S. Cl. ...................................... 604/96; 606/194; 264/DIG. 41; 264/573; 264/523
[58] Field of Search ................... 604/96–103; 606/191–194; 264/523, 526, 531, 534, 573, 573, DIG. 61, DIG. 41

[56] References Cited
U.S. PATENT DOCUMENTS

| B1 4,762,129 | 7/1991 | Bonzel | 606/194 |
|---|---|---|---|
| 4,762,129 | 8/1988 | Bonzel | 128/344 |
| 5,040,548 | 8/1991 | Yock | 128/898 |
| 5,061,273 | 10/1991 | Yock | 606/194 |
| 5,087,246 | 2/1992 | Smith | 604/96 |
| 5,108,415 | 4/1992 | Pinchuk et al. | 604/96 |
| 5,147,302 | 9/1992 | Euteneuer et al. | 604/103 |
| 5,226,887 | 7/1993 | Farr et al. | 604/96 |
| 5,250,069 | 10/1993 | Nobuyoshi et al. | 604/96 |

FOREIGN PATENT DOCUMENTS

0228787 11/1986 European Pat. Off. .... A61M 25/00

Primary Examiner—John D. Yasko
Assistant Examiner—Frank Wilkens, III
Attorney, Agent, or Firm—Dianne M. F. Plunkett; Harold R. Patton

[57] ABSTRACT

A tri-fold dilatation catheter balloon and a method for preparing the same. The disclosed balloon has a tri-fold configuration in which the longitudinal creases defined by three flaps of the balloon are softened to ensure symmetrical deflation of the balloon into its tri-fold form. The tri-fold configuration initially imparted to the balloon by drawing the balloon into an longitudinal interstitial channel defined by three substantially cylindrical pins arranged in a pyramid-type stack. While the balloon is secured within this channel, negative pressure is applied to an inflation lumen of the balloon to deflate the balloon. Negative pressure is maintained on the inflation lumen as the balloon is withdrawn from the interstitial channel, and continues to be maintained while the creases defined by the three tri-fold flaps are heated with a longitudinal heating element. This softens the balloon material in longitudinal creases, so that the same creases will tend form whenever the balloon is deflated. This enhances the reliabilty of symmetrical deflation of the balloon.

4 Claims, 7 Drawing Sheets

TRI-FOLD BALLOON FOR DILATATION CATHETER AND RELATED METHOD

FIELD OF THE INVENTION

The present invention relates to the field of angioplasty, and more particularly relates to a balloon for a dilatation catheter.

BACKGROUND OF THE INVENTION

Percutaneous transluminal coronary angioplasty (PTCA) is widely accepted as an effective treatment of blockages in the coronary arteries. Blockages (stenoses) may occur from cholesterol precipitation on the coronary wall which may be in any stage from initial deposit through aged lesions. Coronary arteries can also become blocked due to formation of thrombus.

The most widely used percutaneous coronary angioplasty makes use of a dilatation balloon catheter. The catheter is inserted into the patient's vascular system and guided until the balloon at the distal end of the catheter is positioned across the stenosis. A radiographic contrast fluid is then fed under pressure through an inflation lumen of the catheter to the balloon, which causes the balloon to expand outward, thereby opening the stenosis.

Various types and configurations of dilatation balloon catheters have been known and used in the prior art. Examples are shown, for example, in U.S. Pat. No. 5,040,548 to Yock, U.S. Pat. No. 5,061,273 to Yock, and in U.S. Pat. No. 4,762,129 to Bonzel (see also Reexamination Certificate No. B14,762,129).

One important characteristic of a dilatation balloon catheter used for angioplasty is its profile, i.e., the outer diameter of its distal end portion when deflated. Considerable effort has been spent in developing low-profile dilatation balloon catheters by minimizing the dimensions of the core or inner tube which extends through the balloon to its distal end, and by reducing wall thickness, to the extent possible, of the balloon itself.

The outer diameter of the deflated distal end portion of a balloon dilatation catheter affects the ease and ability of the dilatation catheter to pass through a guide catheter, through the coronary arteries, and across tight lesions. Application of low-profile balloons can be in a variety of environments, including, but not limited to, over-the-wire, fixed-wire, and monorail systems, as well as with guiding catheters.

A complicating factor in minimizing the deflated profile of a dilatation catheter balloon is that the balloon membrane is typically not distensible, i.e., it does not stretch or contract in response to changes in internal pressure. Thus, the balloon membrane has a constant surface area regardless of whether the balloon is inflated or deflated. Therefore, in order to reduce the outer diameter of the balloon in its deflated condition, it is common to fold the balloon flat, so that two wings or flaps are formed. These two wings are then brought together in some fashion, as by folding or wrapping, so as to reduce the overall diameter of the deflated balloon. Often, some sort of protective sleeve or sheath is disposed around the folded or wrapped balloon to protect the balloon from contamination or damage prior to its use.

In actual use, when inflation fluid is applied to the folded balloon, it causes the flaps to unwrap so that the balloon can inflate to its full inflated state.

While it is desirable to minimize profile, it is also desirable to provide as large as possible an inflated outer diameter of the balloon relative to the deflated profile. One practical effect is that the two flaps formed when the balloon is deflated and prepared for wrapping (during balloon protector installation) become very large relative to the core or inner tube of the catheter. The result is that it is difficult to get these two large flaps to fold together and squeeze out all of the space between them when folded, without damaging the catheter during balloon protector installation.

Various methods and balloon configurations have been proposed in the prior art for providing a dilatation balloon catheter having the lowest profile as possible when deflated and the largest possible diameter when inflated. One approach, which is suggested, for example, in U.S. Pat. No. 5,087,246 to Smith and in U.S. Pat. No. 5,147,302 to Euteneuer et at., is to provide a dilatation balloon having more than two flaps or wings, (for example, three wings) such that when the flaps or wings are wrapped circumferentially, the distance that each flap extends around the catheter is reduced compared with the conventional balloon configuration having only two flaps. The ease with which such flaps fold is also enhanced when their number is increased, such that when the balloon is deflated and withdrawn through the guide catheter following a procedure, the balloon more readily returns to its wrapped condition. The result is a reduced deflated profile given the same inflated diameter.

The above-referenced U.S. Pat. No. 5,147,302 to Euteneuer et al. proposes two different methods for formation of a tri-fold dilatation balloon. In one method, a clamping fixture is used to clamp approximately one-third of the distance across the balloon, this clamped portion defining a first wing or flap. Then the balloon is inflated at low pressure such that the unclamped portion of the balloon is inflated. Finally, pressure is applied against the exterior of the balloon while the balloon is deflated, so that the unclamped portion of the balloon is pressed against the side of the clamp, forming the second and third wings of the balloon.

Another method proposed in the Euteneuer et al. '302 patent involves centering the balloon within a tubular fixture having radially retractable blades circumferentially spaced at 120° intervals. Once the balloon is positioned, the blades are simultaneously moved inward toward the core of the balloon, while a vacuum is applied to the balloon.

Of course, a dilatation balloon must be deflated prior to withdrawal of the dilatation catheter from the patient's vascular system through the guiding catheter used in an angioplasty procedure. It is thus important that the balloon be reliably collapsible to its minimal, radially compact profile. Balloons having only two flaps or wings have proven to be fairly reliable in this regard. Applying negative pressure to the inflation lumen of the catheter causes the balloon to flatten, reforming the two wings. However, as the number of flaps or wings is increased, it becomes more difficult to ensure symmetrical deflation of the balloon.

One method that has been proposed in the prior art for enhancing a balloon's ability to collapse symmetrically is to subject the balloon to heat-treatment when it is initially brought into a multi-fold configuration and wrapped. Such heat-setting approaches have been suggested, for example, in the above-referenced Euteneuer et al. '302 patent and in the above-referenced Smith '246 patent.

While the foregoing may represent some improvement in field of balloon dilatation catheters, the inventor believes that there is an ongoing need for improvements in catheter design and preparation techniques, such that low (deflated) profile and large inflated balloon diameters may be achieved without sacrificing other characteristics, such as reliability of symmetrical deflation.

SUMMARY OF THE INVENTION

The present invention, therefore, is directed to tri-fold dilatation balloons and a method and apparatus for preparing such a balloon.

In accordance with one aspect of the present invention, a method and apparatus is provided for efficiently forming an elongate dilatation balloon into a symmetrical, tri-fold configuration.

In accordance with another aspect of the present invention, a method and apparatus is provided for ensuring that the balloon deflates symetrically into the tri-fold configuration, while at the same time reducing the risk of damage to the balloon.

In one disclosed embodiment of the invention, an elongate balloon is threaded or inserted into an elongate interstitial channel defined by three substantially cylindrical pins. Within the channel, the balloon has a substantially triangular cross-section. Negative (deflation) pressure is applied to the inflation lumen of the balloon, causing the balloon to deflate and collapse into a tri-fold configuration. The deflation pressure is maintained on the balloon as it is withdrawn from the interstitial channel, so that the balloon retains its tri-fold configuration. In the tri-fold configuration, the balloon defines three radial flaps or wings spaced 120° apart, and three longitudinal corners spaced 120° apart between each pair of adjoining flaps. Narrow heating elements are then used to soften the balloon material in each of the corners, thus forming three longitudinal creases in the balloon material. The creases ensure symmetrical deflation of the balloon into the tri-fold configuration. Since only narrow lines along the corners defined between the flaps are heated to produce the creases, the risk of damage to the rest of the balloon as a result of the heating is reduced.

BRIEF DESCRIPTION OF THE DRAWINGS

The foregoing and other features of the present invention will perhaps be best understood with reference to the following detailed description of a specific embodiment of the invention, when read in conjunction with the accompanying drawings, wherein.

DETAILED DESCRIPTION OF A SPECIFIC EMBODIMENT OF THE INVENTION

Figure 1:
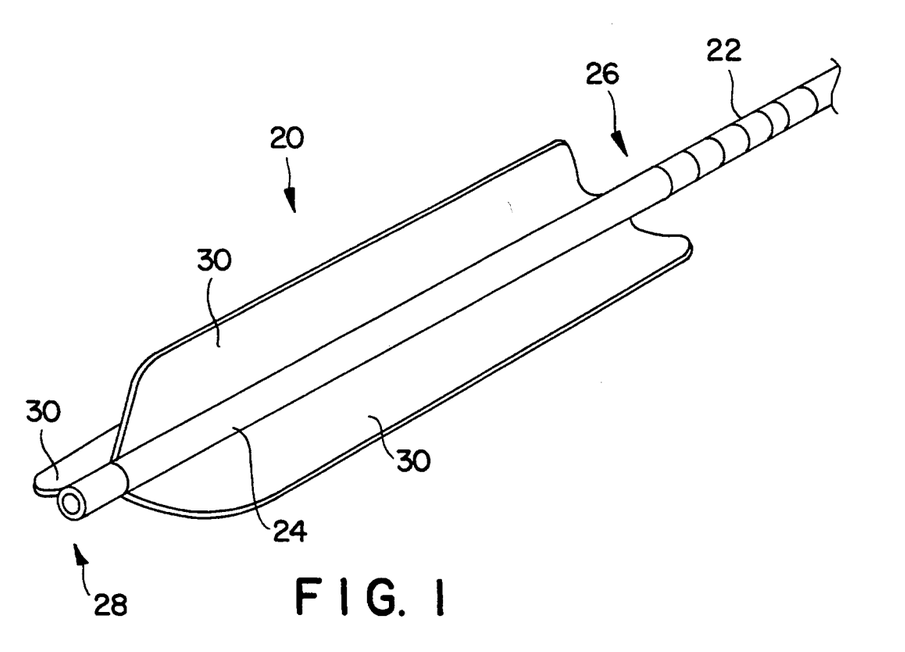
FIG. 1 is an enlarged perspective view of a dilatation catheter balloon in accordance with one embodiment of the invention, shown in an uninflated condition.

Referring to FIG. 1, there is shown an enlarged perspective view of a dilatation catheter balloon 20 in accordance with one embodiment of the present invention. Balloon 20 is preferably made of an elastic biocompatible material such as PE, LLDPE, PET, POC, or the like. Balloon 20 can be made in various sizes, typically ranging from 20 to 30 mm in length, and from 1.5 to 4.0 mm inflated diameter. As shown in FIG. 1, balloon 20 is disposed at the distal end of a dilatation catheter 22 body having an inflation lumen extending therethrough. As will be apparent to those of ordinary skill in the art, this arrangement enables inflation pressure applied at the proximal end of catheter body 22 (not shown) to cause inflation of balloon 20 at the distal end of catheter body 22. In FIG. 1, balloon 20 is shown in a deflated, unwrapped condition.

It is contemplated that, as in some prior art dilatation catheters, catheter body 22 may also include therein or be otherwise associated with an elongate guide wire lumen for accommodating a guide wire used to steer and manipulate balloon 20 within a patient's vascular system during an angioplasty procedure.

Figure 2:
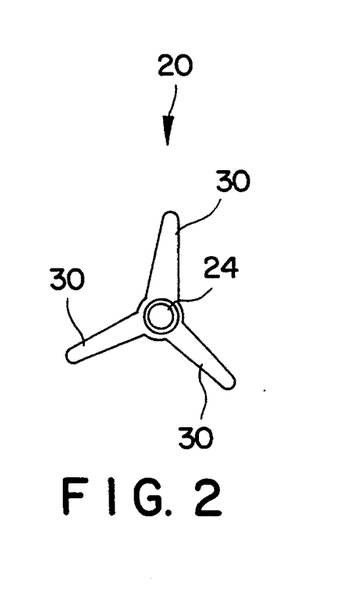
FIG. 2 is an enlarged end view of the dilatation catheter balloon from FIG. 1.

Also shown in FIG. 1 is a core member 24 which extends from the proximal end 26 to the distal end 28 of balloon 20. FIG. 2 is an end view of the balloon from FIG. 1. As can be seen in FIGS. 1 and 2, balloon 20 is of the so-called tri-fold type, as it has three flaps or wings 30 when it is in its deflated condition. As noted above, and as would be appreciated by those of ordinary skill in the art, the provision of multiple (i.e., more than two) flaps in the deflated balloon 20 tends to reduce the profile of balloon 20 when the flaps are wrapped around central core 24.

Figure 3:
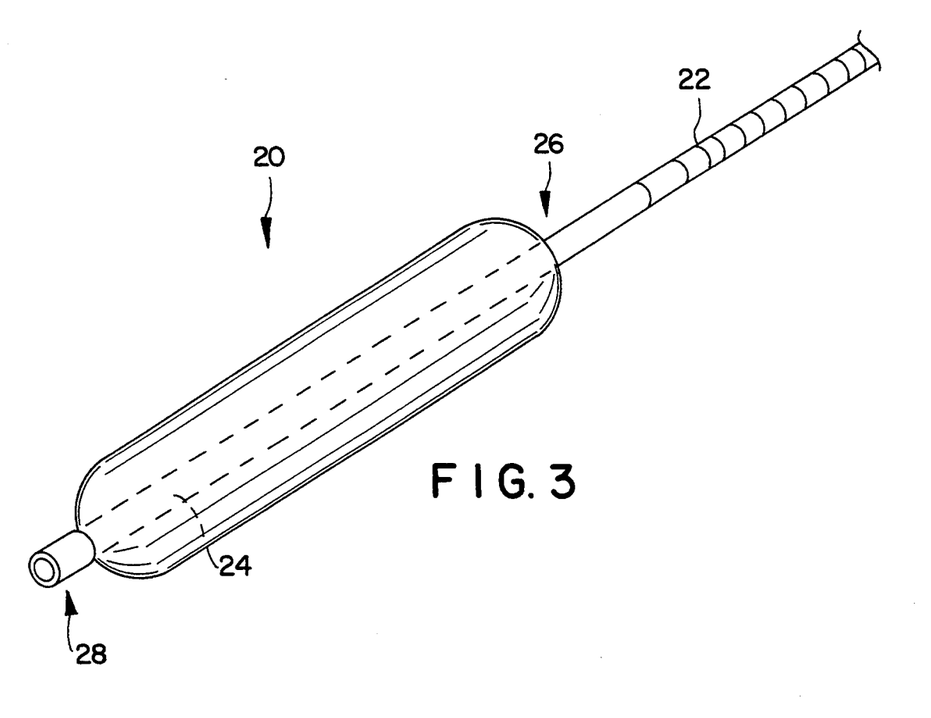
FIG. 3 is an enlarged perspective view of the dilatation catheter balloon from FIG. 1, shown in an inflated condition.
Figure 4:
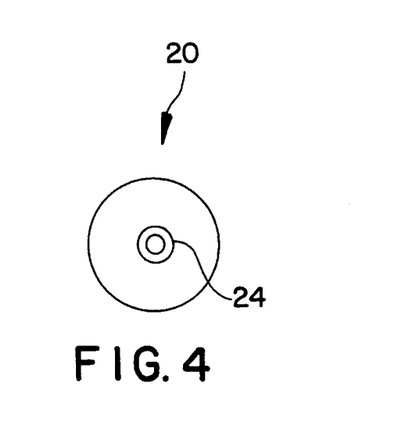
FIG. 4 is an enlarged end view of the dilatation catheter balloon from FIG. 3.

FIGS. 3 and 4 are enlarged perspective and end views, respectively, of balloon 20 in an inflated condition. As shown in FIG. 4, balloon 20, when inflated, has a substantially circular cross section.

Figure 5:
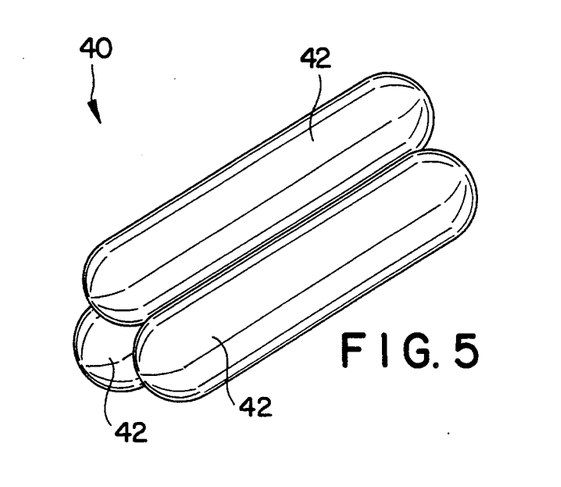
FIG. 5 is a perspective view of a tri-fold formation apparatus in accordance with one embodiment of the invention.
Figure 6:
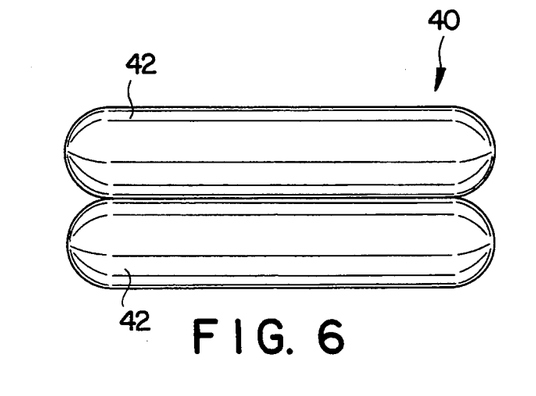
FIG. 6 is a side view of the formation apparatus from FIG. 5.
Figure 7:
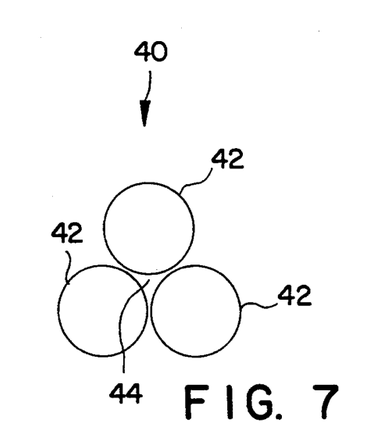
FIG. 7 is an end view of the formation apparatus from FIG. 5.

Turning now to FIGS. 5, 6, and 7, there are shown perspective, side, and end views, respectively of a forming apparatus 40 used in accordance with the presently disclosed embodiment of the invention to initially impart the tri-fold configuration to balloon 20. Forming apparatus 40 comprises three cylindrical pins 42 of equal diameter or asymetrical in configuration, arranged in pyramid-type stack. Pins 42 have smoothly rounded ends. In the presently preferred embodiment of the invention, pins 42 are made of stainless steel or another suitably rigid material.

Figure 8:
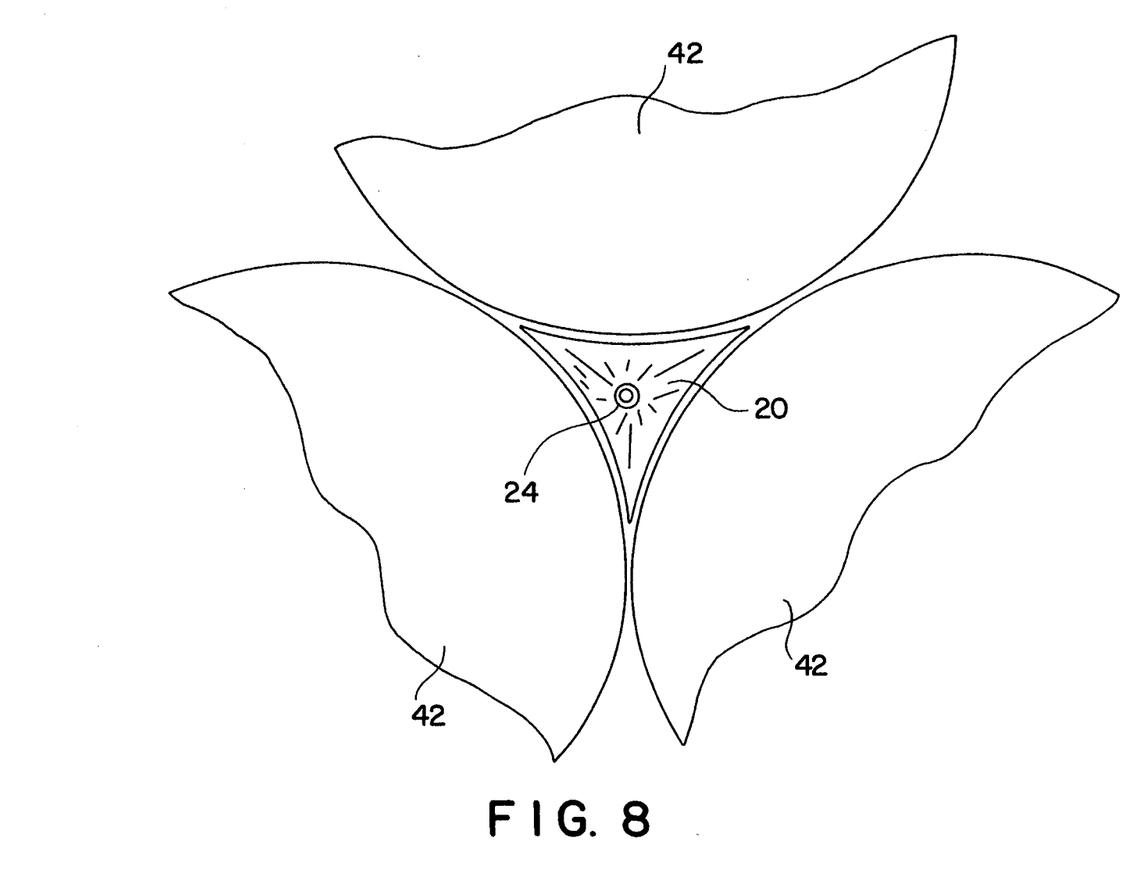
FIGS. 8 and 9 are enlarged end views of a portion of the formation apparatus from FIG. 5 with the balloon from FIG. 1 disposed therein.

With the arrangement shown in FIGS. 5-7, pins 42 define an elongate interstitial channel 44, which is best observed in the end view of FIG. 7. The use of forming apparatus 40 to impart a tri-fold configuration to balloon 20 in accordance with the presently disclosed embodiment of the invention may be best appreciated with reference to FIG. 8, which shows a partially cut-away end view of pins 42. In accordance with one aspect of the present invention, balloon 20 is drawn into interstitial channel 44, as shown in FIG. 8. The flexibility of balloon 20 is such that balloon 20 assumes the substantially triangular shape of interstitial channel 44.

Figure 9:
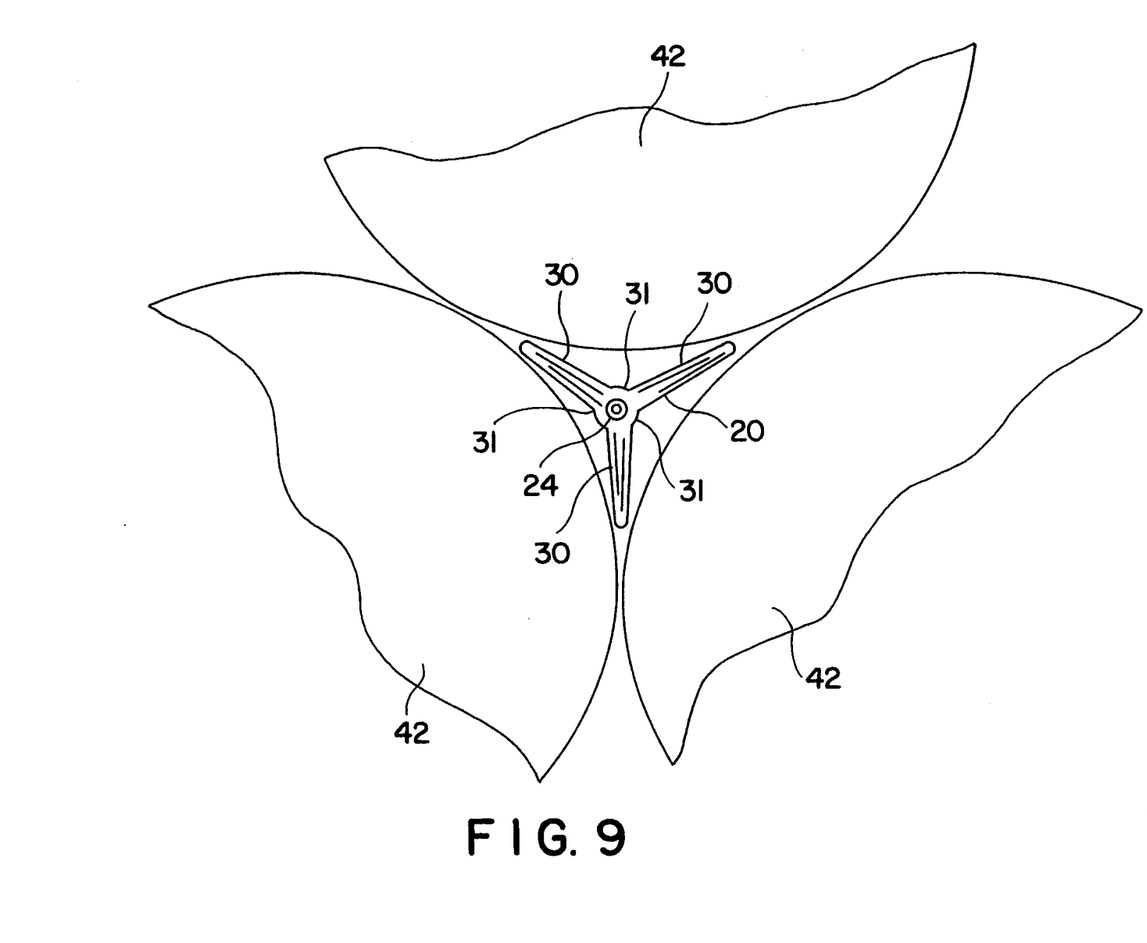

Next, negative pressure (i.e., a vacuum) is applied to the inflation lumen of balloon 20, such that balloon 20 collapses into a tri-fold shape, as depicted in FIG. 9. In the tri-fold configuration, balloon 20 defines three flaps or wings 30, radially oriented with respect to inner core 24 and oriented 120° apart from one another. Each pair of wings 30, in turn, defines one of three elongate corners 31, which are similarly oriented 120° apart.

As long as negative pressure is maintained on the inflation lumen of balloon 20, balloon 20 will remain in the tri-fold configuration shown in FIG. 9. Thus, balloon 20 can be withdrawn from interstitial channel 44 and subjected to the next stage of the formation process.

Figure 10:
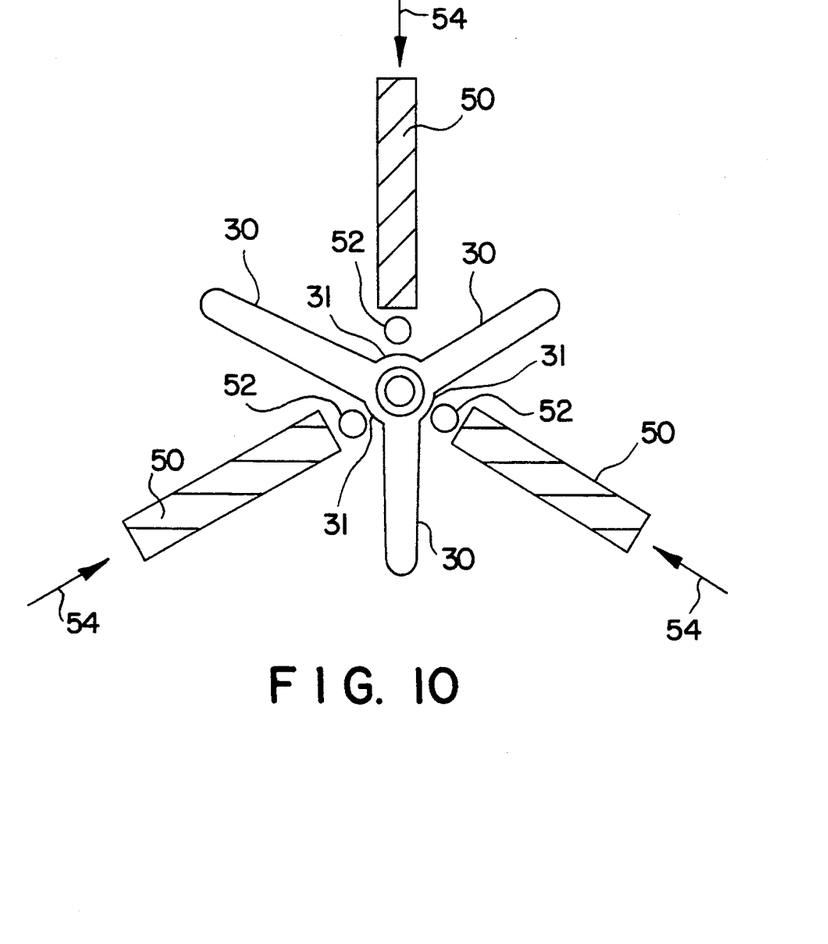
FIG. 10 is a top view of a heating fixture in accordance with one embodiment of the invention, with the balloon from FIG. 1 disposed therein.

In particular, and with reference now to FIG. 10, the next stage in the formation process is to soften the material in each of the elongate corners 31, so that balloon 20 will be creased and thus retain its shape even after negative pressure is removed from its inflation lumen. In accordance with the presently disclosed embodiment of the invention, this is accomplished through the use of a heating fixture comprising three radial members designated as 50 in FIG. 10.

Members 50 are radially oriented 120° apart from one another. Each radial member 50 has coupled on its inner end a heating element 52. In the presently disclosed embodiment of the invention, heating elements 52 each consist of a single electrical resistance heating wire, similar to those found in ordinary household toasters, for example.

Radial members 50 are radially moveable with respect to a central region in which balloon 20 is disposed. As balloon 20 is brought into position within this central region, radial members 50 press heating elements 52 against corners 31 in balloon 20. That is, heating elements are pressed into corners 31 with pressure in the direction of arrows 54 in FIG. 10 exerted by radial members 50. Each separate one of heating elements 52 is thus brought into contact with a different one of the three corners 31 defined by tri-folded balloon 20. In accordance with an important aspect of the present invention, the heat from heating elements 52 softens the balloon material in corners 31 to form creases, but advantageously does not affect any other balloon material. The chance of damage to the rest of the balloon material is therefore significantly reduced as compared with prior art heat-treating procedures in which the entire balloon is subjected to high temperatures, or by the use of stretching techniques, as described in U.S. Pat. No. 5,087,246.

Figure 11:
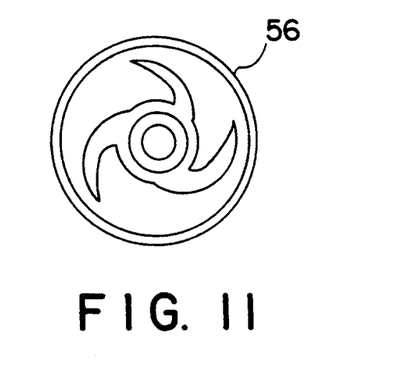
FIG. 11 is an end view of the balloon from FIG. 1 being spiral wrapped.

After radial members 50 are retracted radially outward, balloon 20 can be removed from the heating fixture, and the negative pressure can be removed from the balloon's inflation lumen. Balloon 20 is then ready for spiral-wrapping and heat-setting, as depicted in FIG. 11 and in accordance with common practice in the art. As shown in FIG. 11, a heat-set sleeve or protector 56 may be provided during the heat-setting operation, in accordance with common practice in the art.

Figure 12:
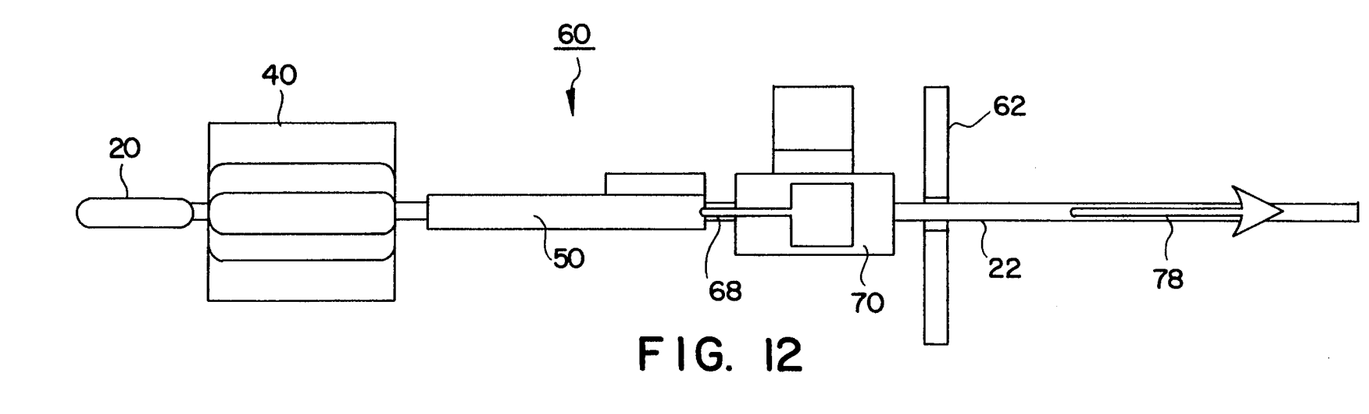
FIG. 12 is a top view of an apparatus incorporating the tri-fold formation apparatus of FIG. 5 and the heating fixture of FIG. 10.
Figure 13:
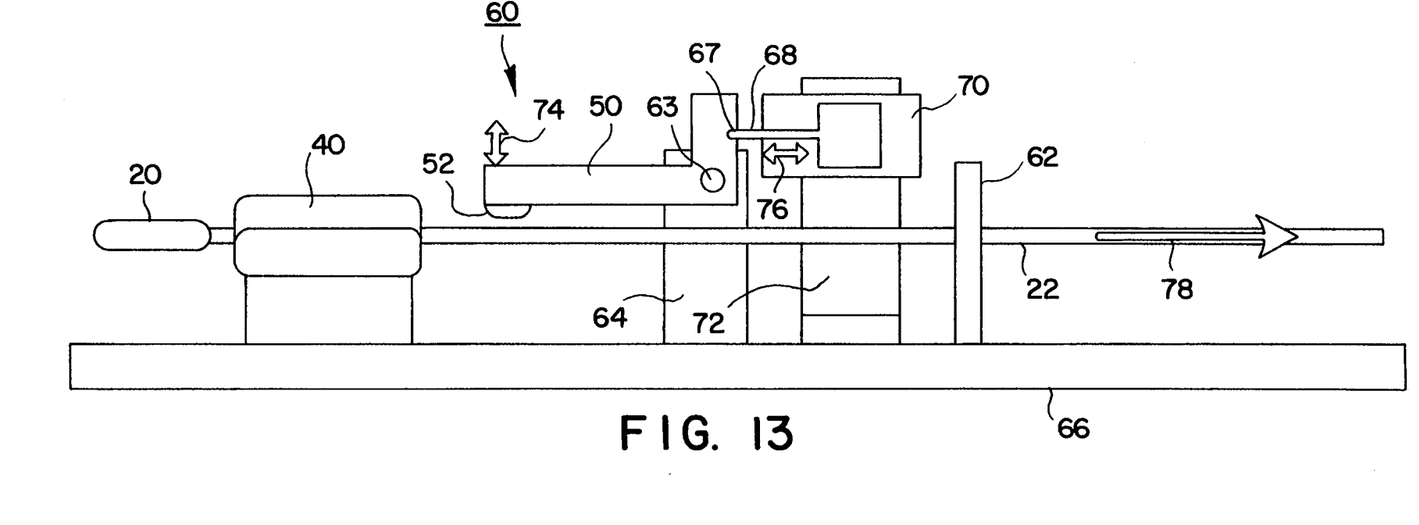
FIG. 13 is a side view of the apparatus of FIG. 12.

Thus far, the present invention has been described in terms of balloon 20 being drawn through the formation apparatus previously described with reference to FIG. 5 and then having its tri-fold creases heated and softened, as described above with reference to FIG. 10, to ensure reliable symmetrical deflating of balloon 20. In FIGS. 12 and 13 there are shown top and side views, respectively, of an apparatus 60 which, in accordance with the presently preferred implementation of the invention, incorporated both formation apparatus 40 of FIG. 5 and the heating fixture of FIG. 10.

It is to be understood that elements of apparatus 60 which are identical to elements shown in FIGS. 1–11 have retained identical reference numerals in FIGS. 12 and 13. Thus, for example, FIGS. 12 and 13 show a dilatation balloon 20 disposed at the distal end of a catheter body 22. In FIGS. 12 and 13, catheter body passes through formation apparatus 40 and past the heating fixture comprising radial members 50 and heating elements 52.

For the sake of clarity, only one radial member 50 is depicted in FIGS. 12 and 13; it is to be understood, however, that three radial members 50 are provided, spaced apart 120° from each other. As shown in FIG. 13, radial member 50 has a heating element 52 disposed at one end thereof. At the other end, radial member 50 is pivotally coupled, at pivot point 63, to a support 64. Support 64 is rigidly secured to a base 66. Also coupled to radial member 50, at a pivot point 67 is the piston rod 68 of an actuator 70. In the presently preferred embodiment of the invention, actuator 70 is a Airpot TM dashpot, commercially available from Airpot Corp., Norwalk, Conn. Actuator 70 is rigidly supported by a supporting member 72 attached to base 66.

Those of ordinary skill in the art will appreciate that as a result of the pivotal arrangement of radial arm 50 shown in FIG. 13, left and right motion of actuator piston rod 68 (i.e., movement of piston rod 68 in the directions indicated by arrow 76 in FIG. 13) is translated into up and down movement of the end of radial member 50 (i.e., movement of radial member 50, and hence of heating element 74, in the directions indicated by arrow 74 in FIG. 13). Actuator 70 is coupled to a pressure regulator (not shown), such that the movement of radial member 50 can be controlled. Also, as will be hereinafter described in greater detail, the force with which heating element 52 is pressed against balloon 20 to form creases 31 can be controlled.

In using apparatus 60, first the proximal end of catheter body 22 is threaded through interstitial channel 44 of formation apparatus 40. Catheter body also passes through a guide member 62. Catheter body 22 is also shown in FIG. 13 passing by radial member 50 in the heating fixture. Again, it is to be understood that two other radial members 50, not shown in FIGS. 12 and 13, would be similarly positioned around catheter body 22 passing through apparatus 60. Next, catheter body 22 is pulled or drawn in the direction of arrow 78 in FIG. 13. As a result, balloon 20 is pulled into interstitial channel 44 of formation apparatus 40, as previously described with reference to FIG. 8. It is contemplated that while this is being done, balloon 20 may be lightly inflated, e.g., inflated to 1 PSI or so, from the proximal end of catheter body 22.

Next, negative (deflation) pressure is applied to the proximal end of catheter body 22, so that balloon 20 collapses into a tri-fold configuration, as previously described with reference to FIG. 9.

While negative pressure is maintained, catheter body 22 is drawn further in the direction of arrow 78, so that balloon 20 is drawn past heating elements 52 on radial members 50. Actuators 70 associated with each radial member 50 ensure that heating elements 52 are pressed against corners 31 in balloon 20 with a predetermined and controlled force. This prevents damage to balloon 20. As corners 31 are drawn past heating elements 52, the balloon material is softened somewhat to form creases which will cause balloon 20 to tend to collapse into a tri-fold shape when deflated.

After balloon 20 has passed by heating elements 52, catheter body 22 can then be pulled even further in the direction of arrow 78, pulling balloon 20 free of apparatus 60. Balloon 20 is then ready for wrapping and heat-setting, as previously described with reference to FIG. 11.

From the foregoing detailed description of a particular embodiment of the invention, it should be apparent that a tri-fold dilatation catheter balloon, and a method and apparatus for making it, have been described. Although a specific embodiment of the invention has been described herein in some detail, this has been done for illustrative purposes only, and is not intended to be limiting with respect to the scope of the invention. It is contemplated that various substitutions, alterations, and/or modifications, including but not limited to those specifically discussed above, may be made to the embodiment of the invention disclosed herein without departing from the spirit and scope of the present invention as defined in the appended claims, which follow.

What is claimed is:

1. A method for preparing an elongate tri-fold dilatation catheter balloon, comprising the steps of:
    (a) drawing said balloon into an elongate interstitial channel defined by three substantially cylindrical pins;
    (b) applying negative pressure to a lumen of said balloon to deflate said balloon into a tri-fold configuration;
    (c) removing said balloon from said interstitial channel while maintaining said negative pressure;
    (d) softening said balloon along three longitudinal lines evenly spaced around said elongate balloon.

2. A method in accordance with claim 1, wherein said step of softening comprises pressing a longitudinally-oriented heating wire against said balloon along each of said longitudinal lines.

3. A method in accordance with claim 1 wherein said step of drawing said balloon into an elongate interstitial channel comprises a channel which is triangular in cross section.

4. A method in accordance with claim 2 wherein said balloon is folded to display three wings and said balloon is heated only in areas intermediate to said wings.

* * * * *